(12) United States Patent
Nordgren

(10) Patent No.: US 8,092,432 B2
(45) Date of Patent: Jan. 10, 2012

(54) OUTDWELLING SLIT VALVES AND ASSEMBLIES FOR MEDICAL LIQUID FLOW THROUGH A CANNULA AND RELATED METHODS

(75) Inventor: Greg Nordgren, Coralville, IA (US)

(73) Assignee: Nordgren Corporation, Coralville, IA (US)

( * ) Notice: Subject to any disclaimer, the term of this patent is extended or adjusted under 35 U.S.C. 154(b) by 170 days.

(21) Appl. No.: 12/455,244

(22) Filed: May 29, 2009

(65) Prior Publication Data

US 2009/0259175 A1    Oct. 15, 2009

Related U.S. Application Data

(63) Continuation-in-part of application No. 11/121,342, filed on May 3, 2005, now abandoned.

(51) Int. Cl.
*A61M 5/00*      (2006.01)

(52) U.S. Cl. .......... 604/247; 604/30; 604/246; 604/256; 604/537; 137/843

(58) Field of Classification Search .................... 604/30, 604/34, 167.01–167.04, 246, 247, 256, 533, 604/537; 137/843, 845, 846; 251/149.1
See application file for complete search history.

(56) References Cited

U.S. PATENT DOCUMENTS

| | | |
|---|---|---|
| 703,101 A | 6/1902 | Ware |
| 2,069,105 A | 1/1937 | Engle ............................. 152/12 |
| 2,629,393 A | 2/1953 | Langdon ....................... 137/217 |
| 3,525,357 A | 8/1970 | Koreski .................... 137/516.11 |
| 3,620,500 A | 11/1971 | Santomieri ................ 251/149.1 |
| 3,941,149 A | 3/1976 | Mittleman ................. 137/493.1 |
| 4,084,606 A | 4/1978 | Mittleman ..................... 137/102 |
| 4,143,853 A | 3/1979 | Abramson ................. 251/149.1 |
| 4,341,239 A | 7/1982 | Atkinson ...................... 137/493 |
| 4,434,810 A | 3/1984 | Atkinson ...................... 137/493 |
| 4,535,818 A | 8/1985 | Duncan et al. ................ 137/846 |
| 4,535,819 A | 8/1985 | Atkinson et al. ............. 137/846 |
| 4,566,493 A | 1/1986 | Edwards et al. ............. 137/846 |
| 4,671,796 A | 6/1987 | Groshong et al. ............ 604/247 |
| 4,883,456 A | 11/1989 | Holter .............................. 604/9 |
| 4,968,294 A | 11/1990 | Salama ........................... 600/30 |
| 4,995,863 A | 2/1991 | Nichols et al. ................ 604/247 |
| 5,033,504 A | 7/1991 | Kallenbach ................. 137/493.1 |
| 5,112,301 A | 5/1992 | Fenton et al. .................... 604/30 |
| 5,169,393 A | 12/1992 | Moorehead et al. .......... 604/247 |
| 5,984,903 A | 11/1999 | Nadal ........................... 604/256 |
| 2002/0121530 A1 | 9/2002 | Socier ........................... 222/494 |
| 2004/0102738 A1 | 5/2004 | Dikeman et al. ............. 604/256 |

*Primary Examiner* — Kevin C Sirmons
*Assistant Examiner* — Emily Schmidt
(74) *Attorney, Agent, or Firm* — Lynn G. Foster

(57) ABSTRACT

Novel outdwelling normally closed bulbous medical bidirectional slit valves and outdwelling slit valve assemblies for influent and effluent fluid flow into and from a medical patient are disclosed, as well as related methods.

8 Claims, 5 Drawing Sheets

OUTDWELLING SLIT VALVES AND ASSEMBLIES FOR MEDICAL LIQUID FLOW THROUGH A CANNULA AND RELATED METHODS

This application is a continuation-in-part of U.S. patent application Ser. No. 11/121,342 filed May 3, 2005 now abandoned.

FIELD OF INVENTION

The present invention relates generally to outdwelling control of medical bidirectional liquid flow in a cannula and, more particularly, to novel normally closed outdwelling slit valves and slit valve assemblies and related methods for selective slit valving of medical liquid flow in either of two directions at any point in time along the hollow cannula, which may be a catheter tube, where the aspirating flow rate is less than the infusing flow rate.

BACKGROUND

Outdwelling slit valves have been proposed in the past. For example, see U.S. Pat. Nos. 5,201,722 and 5,984,902, which disclose transversely directed disc-shaped slit valve diaphragms each having a central slit, the axial flexural displacement of which is mandatorily constrained by abutment structure fore and/or aft of each transverse disc-shaped diaphragm. Prior outdwelling slit valves leave unanswered problems of interior dead space, provision of greater rates of flow without compromising the level of back pressure, and lack valve integrity.

Outdwelling valves of the type in question have been prone to low flow rates due to the region in which a slit valve can be placed within a disc, for example, and still have enough space to securely hold the disc in position. The placement of the slit valve disc is often unstable, being prone to being dislodged under higher than normal pressures, causing the slit valve to either malfunction or perform poorly. In some outdwelling slit valves the limited space is used to add features like extra valves to work in one direction or the other, which lowers the performance of the valve.

BRIEF SUMMARY AND OBJECTS OF THE INVENTION

In brief summary, the present invention overcomes or substantially alleviates the past problems of low flow rates and the inability to handle high pressure imposed on the valve. One or more novel outdwelling cup-shaped slit valves and outdwelling slit valve assemblies are provided, as well as related methods. The problems of increased flow rates and valve integrity, without compromising back pressure are addressed by the present invention. Normally closed hollow male bulbous medical bidirectional slit valves are disclosed, which under certain pressure differential, will yawn differently to open a slit to a greater or lesser extent to accommodate greater influent flow than effluent flow.

With the foregoing in mind, it is a primary object to overcome or substantially alleviate past problems in cannula-related medical slit valve field.

Another paramount object is the provision of one or more novel outdwelling cup shaped medical slit valves, outdwelling slit valve assemblies and related methods.

A further valuable object is the provision of novel outdwelling medical bidirectional slit valves, slit valve assemblies and related methods, which address the problems of dead space and increased flow rates without compromising the adequacy of the back pressure.

An additional object of critical importance is the provision of normally closed hollow male bulbous medical bidirectional slit valves which, responsive to various pressure differentials open to slit to a greater or lesser extent to accommodate greater influent flow than effluent flow.

These and other objects and features of the present invention will be apparent from the detailed description taken with reference to accompanying drawings.

BRIEF SUMMARY AND OBJECTS OF THE INVENTION

DETAILED DESCRIPTION OF THE ILLUSTRATED EMBODIMENTS

Figure 1:
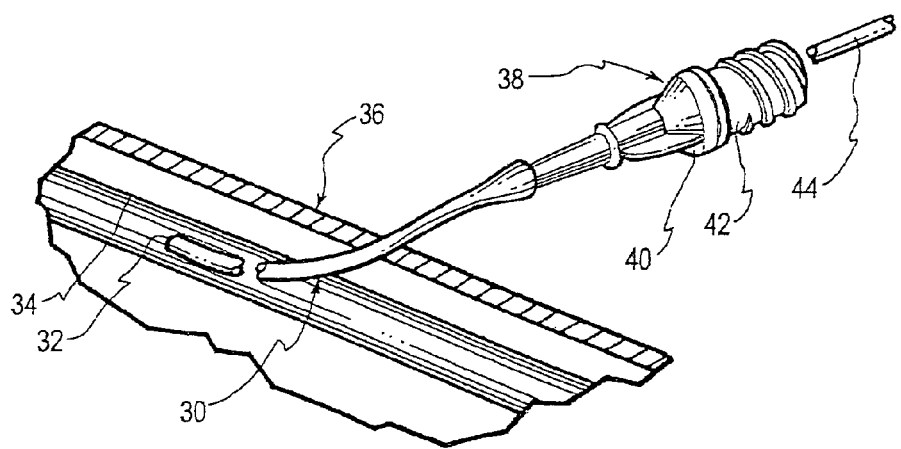
FIG. 1 is a diagrammatic representation of one outdwelling slit valve assembly in accordance with the present invention for infusion and aspirating into and from an internal cavity of a medical patient.
Figure 2:
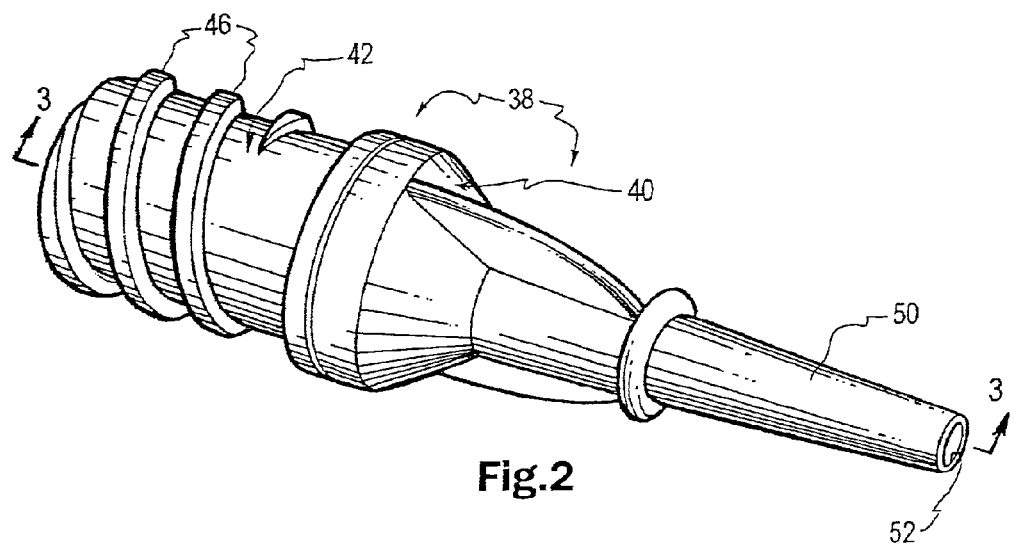
FIG. 2 is a perspective of a two-part housing in which a slit valve, embodying principles in accordance with the present invention, is contained.

The present invention solves or reduces past problems primarily in the catheter-related cardiovascular slit valve field, but also applicable to the human respiratory system and other body cavities. One or more normally closed cup-shaped slit valves, which may be in a variety of forms, are outdwelling, being disposed remote from the distal end of each catheter tube of a medical patient whereby problems of the past are greatly reduced, if not eliminated. The term outdwelling is used to mean placement of the slit valve at the proximal end of a cannula, the distal end of which is disposed within a body cavity for fluid flow purposes. Thus, the term outdwelling embraces both placement of the slit valve outside the body of a patient or placed subcutaneously at a non-cavity site for safety purposes only, such as in conjunction with an implanted port to control, at the proximal end of a cannula, the flow of liquid from the port to a body discharge site remote from the port and the slit valve. The slit valves, in proximal regions of catheter tubes, comprise one or more normally closed slit valves disposed in a two-part housing. The slit valves accommodate bidirectional flow. By two-way, it is meant that a given proximal outdwelling slit-valve both aspirates and infuses fluid, respectively, at different points in time from and into the associated catheter tube or cannula.

Accordingly, an outdwelling cup-shaped slit valve may comprise from one normally closed slit up to several normally closed slits, located on planar distal flats. It is not necessary that all slits have the same length or thickness, but the slit sites are centrally thinner than other parts of the slit valve. Some may extend into or across the apex or tip of the nipple-shaped slit valve. The slits may also extend into the wall of the central portion of the slit valve to assist in providing greater infusion flow compared to aspiration flow.

The preferred materials for forming the slit component of the slit valve comprise medical grade silicone rubber, polyurethane and other suitable natural and synthetic elastomeric materials. The other components of the slit valve may comprise medical grade synthetic resinous or elastomeric materials. The material comprising each slit component must have sufficient flexibility for the slit lips forming the normally closed slit to flex inwardly and outwardly, respectively, when predetermined pressure differentials are imposed on the slit diaphragm, in order to accommodate fluid flow in the direction desired. Treating the slit lips with a softening composition is known in the art and may take place to provide the desired flexibility.

The slit in the cup-shaped slit valve may be disposed transversely or radially or diagonally or otherwise, as deemed most appropriate by those having skill in the art. Opposing slit valves located on different sides of the distal end of a slit valve may be used.

This invention comprises a slit valve located in a cup-shaped hub attached at the proximal end of a catheter, the distal end of which is indwelling. For example, the catheter may be used to control fluid flow in and out of the body. Infusaids, such as saline, blood, hyper alimentation, or any medication prescribed for a patient, may be administered intravenously through the catheter. A paramount purpose of slit valves according to the present invention is to provide safety to the patient while the catheter is in use. Pressures inside and outside of the body have been known to cause blood to enter the catheter, which may clot or allow air in an open system to enter the body. Since the early 1908's valves of different types have been employed on the distal end (indwelling) of catheters and more recently certain types of proximal valves have been devised. Slit valves of the present invention have more flexibility to withstand pressures and allow greater controllability of the opening and closing of the slit valves during times of use and non-use when protection is needed.

Several configurations of this invention are disclosed. In all of these configurations there is at least one normally closed slit located in a flat of an outdwelling cup-shaped slit valve. The location, length of each slit and wall thickness allow for variation in valve functions. For instance, the varying of the slit wall thickness and or slit length has an effect, to some extent, on the pressure differential required to open the valve. The use of more than one slit in planar flat locations will affect flow, but not necessarily opening or closing pressures. Also, one slit, which transverses two or more valve flats can impact opening pressures in one direction and not the other. Material properties also have an effect on the opening and closing of valves, i.e., if the material is soft, the valves will act different than if the material is of higher durometer. This creates the ability to adjust the configuration of the slit valve or valves and select a material to produce an effective valve for the purpose intended.

The present invention accommodates the following:

1. Use of one or more slits, each slit extended through an outside flat surface to opposite inner flat surface. Each slit is essentially at least as long as the outer planar flat surface in which the slit is located. The slit may however extend beyond the flat surface across the adjoining apex or tip and/or into the wall of the central portion of the slit valve.
2. Each valve accommodates bi-directional flow under certain conditions. In other words, fluid can flow in either of two directions through the slit. At any point in time when at rest, the slit valve remains normally closed, as is true when pressures are under the pressure differential needed to open the valve in one direction or the other.
3. The slits of the present slit valves flex or yawn into oppositely open positions so as to provide a greater influent (infusion) flow than an effluent (aspiration) flow.
4. The difference in valve opening pressures on each side of the valve allows the valve, when closed, to hold back both positive and negative cardiovascular pressures. The vascular system creates higher positive pressures than negative pressures so the valve accommodates this difference to open effectively in both directions when the predetermined differential pressures are respectively reached.
5. Where more than one slit in a given valve is used, the slits may work simultaneously or separately one from the other, but each operates on its own responsive to the desired pressure differential. The benefit is more total slit length accommodating more flow in either direction, without compromising performance.
6. The end portion of various slit components (diaphragms) of the slit valves may be shaped differently to create the longer slits, which may increase flow rates, but also allow the slit tips to be flexed in such a way as to provide different distal and proximal flow rates through the same slit.
7. In all of the slit components, the slit thickness extends between two flat parallel surfaces comprising a thin planar flat. The inner flat surface may be smaller than the outer flat surface so the flex is greater in the distal direction than the proximal direction. A slit extending the length of the outer flat surface (or beyond) will, therefore, open to a larger extent than when opened inwardly. This allows the opening pressure to be lower when flexed in the outward direction than when opened in the inward direction.

Reference is now made to the drawings, wherein like numerals are used to designate like parts throughout. Any normally closed cup-shaped outdwelling slit valve of this invention may be used for infusing and aspirating and may be any of several configurations. Each of the cup-shaped slit valves shown in the Figures comprises one-piece construction, with each slit valve typically placed within an outdwelling housing positioned external of a medical patient in a proximal relation to a hollow cannula, which selectively accommodates fluid flow to and from a medical patient.

FIG. 1 is intended to be representative of placement of outdwelling slit valves in accordance with the present invention external, i.e. outdwelling of the medical patient where a hollow cannula 30 comprising an open end 32 is disposed within a body cavity 34 of a medical patient 36. The slit valve of FIG. 1 is concealed within a housing, generally designated 38, comprising interconnected distal and proximal housing parts 40 and 42. The slit valve within the housing 38 accommodates selective fluid flow into and from the patient 36, based upon the slit valve being subjected to a predetermined pressure differential, i.e., the difference between the pressure on the distal side in tube 30 and the pressure on the proximal side in tube 44. While in most instances, the body cavity 34 is a cardiovascular vein, where the fluid flow comprises liquid displacement, liquid displacement in other body cavities is contemplated, as is gaseous flow from and to other body cavities.

FIGS. 2-5 illustrate additional views of the two-part housing 38 of FIG. 1 and a cup-shaped slit valve 60 within the housing 38. The exterior of the proximal housing part 42 comprises an exposed luer lock thread 46 and a hollow interior 48 to accommodate selective fluid flow. Thread 46 accommodates luer lock threaded connection with a luer lock fitting at the distal end of hollow proximal tube 44 (FIG. 1) in a conventional manner. Distal housing part 40 comprises a tapered elongated tip 50 sized to accommodate a press-fit overlapping connected relationship with the proximal end of the cannula 30, the cannula 30 being illustrated as a hollow catheter tube of synthetic resinous material of medical grade having a distal opening 32 (FIG. 1). The interior of the distal housing part 40 comprises the hollow passageway 52 accommodating selective fluid flow and an enlarged slit valve receiving compartment 54.

The proximal and distal housing parts 42 and 40 are connected at interface 56 in an interlocking male-female relationship, with or without a bonding agent, as determined by those skilled in the art. Thus, when assembled as shown in FIG. 3, the housing parts 40 and 42 may be either separable or inseparable.

Figure 3:
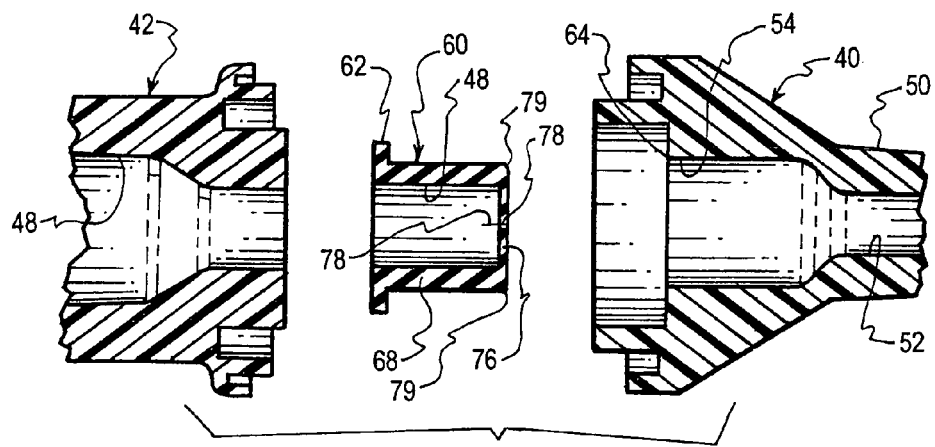
FIG. 3 is an exploded cross-section taken along the lines of 3-3 of FIG. 2.

Contained in compartment 54, as shown in FIG. 3, is a one-piece normally closed cup-shaped blunt end slit valve, generally designated 60. The slit valve 60 comprises a proximal flange 62, which, when assembled, is compressively trapped between and compressively secured between the two housing parts 40 and 42, as best shown in FIG. 3. FIG. 3 illustrates flange 62 is firmly retained between a distal shoulder 64 of housing part 40 and proximal shoulder 66 of housing part 42. The central portion 68 of the slit valve 60 is annular at the outside and the inside at hollow 48.

Figure 4:
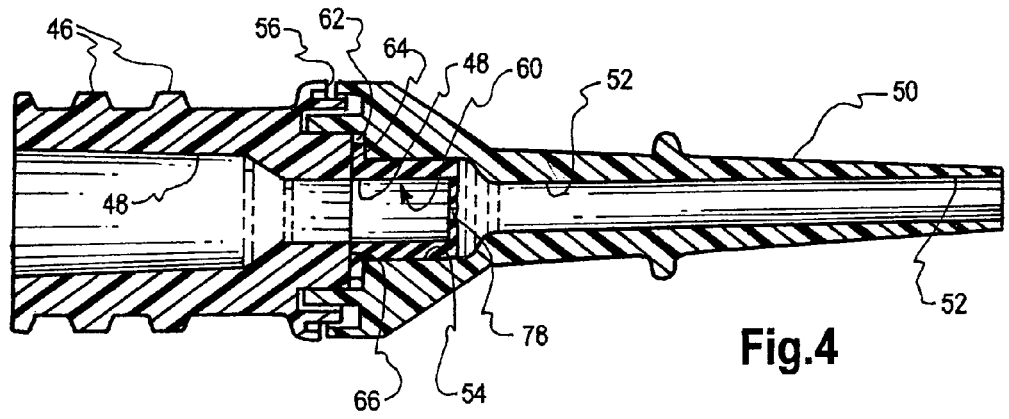
FIG. 4 is an assembled cross-section of the assembly of FIG. 3.
Figure 5:
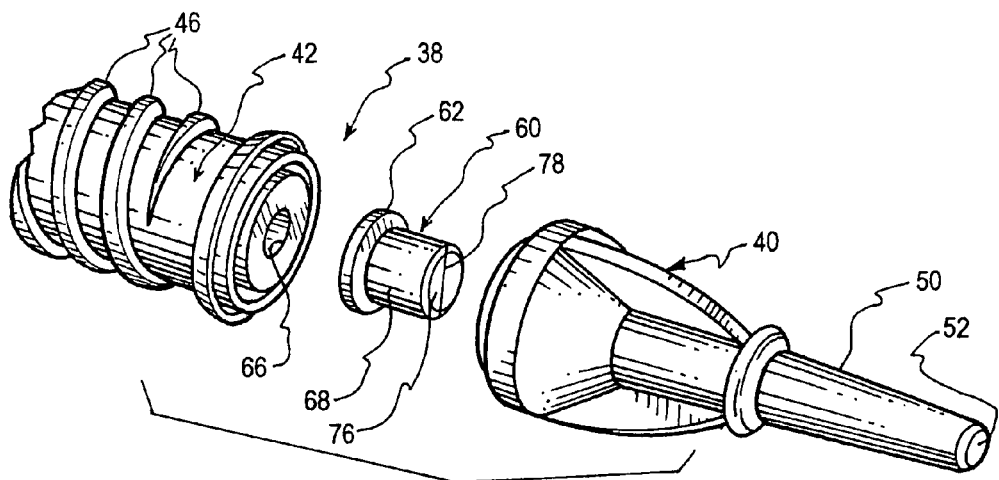
FIG. 5 is a fragmentary exploded perspective of the slit valve assembly of FIG. 2.

The blunt end-cup-shaped slit valve 60 comprises annular hollow central portion 68 of essentially uniform inside and outside diameter ending in a blunt thin wall tip 76. The distal end at tip 76 is equipped with at least one normally closed radially directed slit 78 comprised of opposed flexible normally contiguous lips 80 (FIGS. 15-18). The slit 78 is placed in a flat region (a flat) of the slit valve. Where only one slit is used in the slit valve, that slit may wrap around annular corner 79 and extend into the annular wall 68 as shown in FIGS. 3-5 and thus accommodate greater infusion than aspiration fluid flow, as shown in FIGS. 5-18, when predetermined pressure differentials are reached.

Figure 6:
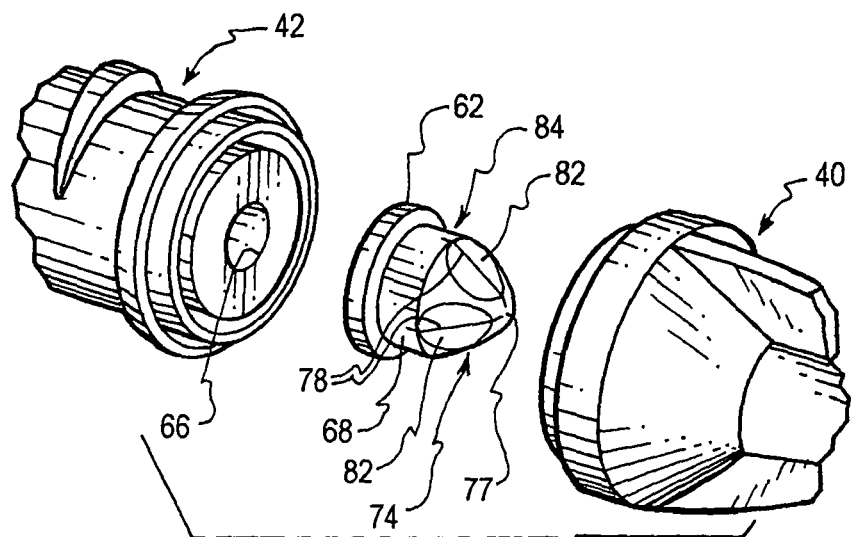
FIG. 6 is a fragmentary exploded perspective of a split valve assembly similar to FIG. 5 but including a different slit valve component.

The slit valve 84 of FIG. 6 is comprised of the previously-described proximal flange 63, a shorter central annular portion 68 and a tapered distal portion 74, but comprised of four flats 82, each flat being equipped with a diagonally disposed slit 78. Each slit extends from the distal tip 77 proximally and diagonally a short distance into the annular central portion 68. Any of the four slits 78 of cup-shaped slit valve 84 is sized, shaped and formulated to accommodate influent infusion and effluent aspiration when, in each case, a threshold pressure differential is reached to accommodate fluid flow. The threshold pressure differential necessary to operate each slit valve of FIG. 6 may be the same or different, as determined those of skill in the art, taking into account the intended function of each slit valve.

Figure 7:
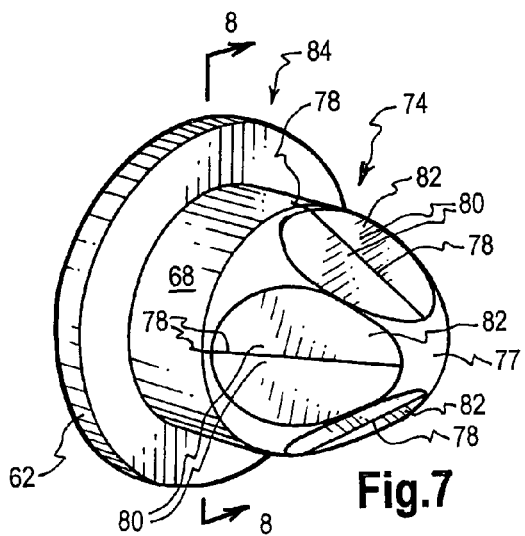
FIG. 7 is an enlarged perspective of the nipple-shaped slit valve component shown in FIG. 6.
Figure 8:
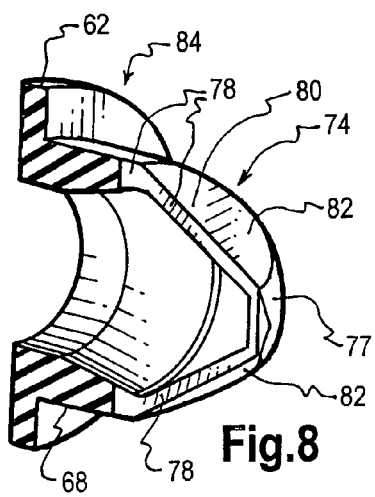
FIG. 8 is a perspective with parts shown in cross-section taken along lines 8-8 of FIG. 7.
Figure 9:
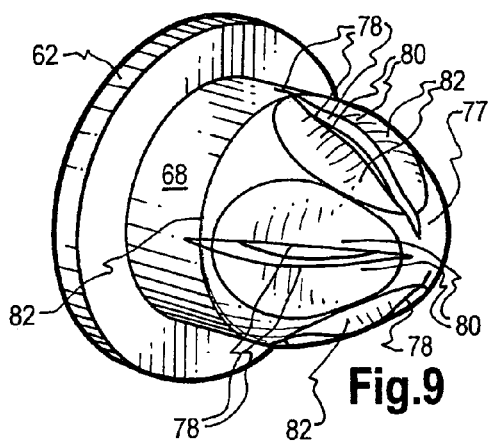
FIG. 9 is a perspective of the slit valve component of FIG. 7, shown flexed so as to accommodate a greater infusion flow.
Figure 10:
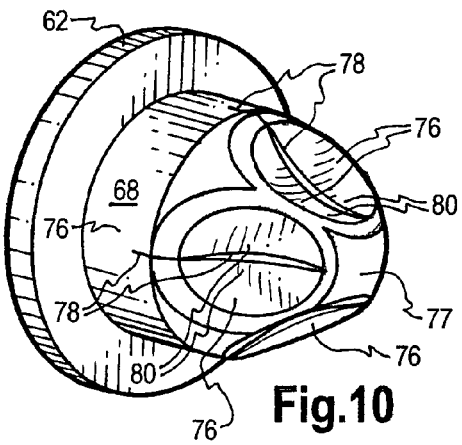
FIG. 10 is a perspective of the slit valve component of FIG. 7, shown flexed so as to accommodate a lesser aspiration flow.

The slit valve 84 is shown in its normally closed configuration in FIG. 7-8 and flexed by pressure differential into an open effluent flow configuration in FIG. 9 and an open influent flow configuration in FIG. 10.

Figure 11:
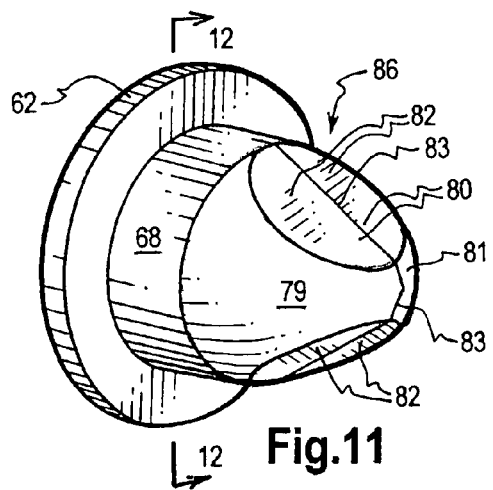
FIG. 11 is perspective of another nipple-shaped slit valve embodiment.
Figure 12:
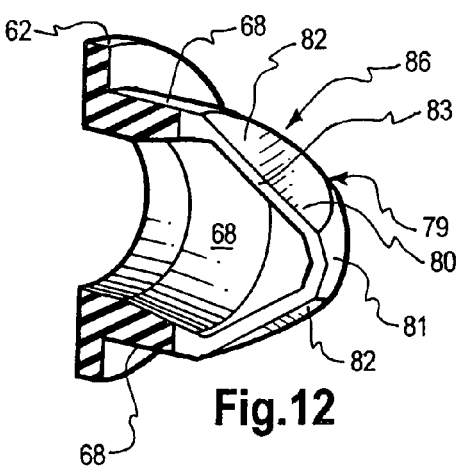
FIG. 12 is a perspective with parts shown in cross-section taken along lines 12-12 of FIG. 11.
Figure 13:
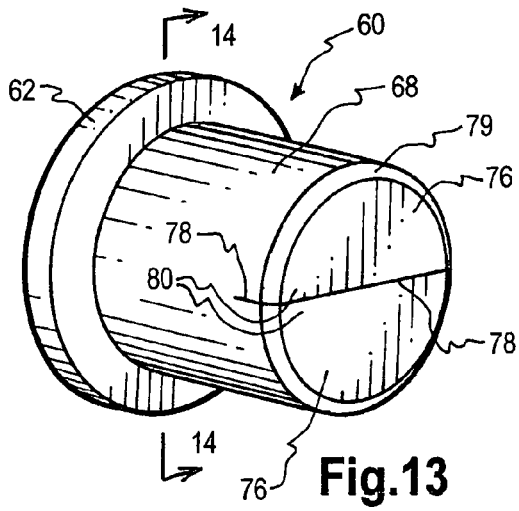
FIG. 13 is a perspective of the nipple-shaped valve component of FIGS. 3 and 4.
Figure 14:
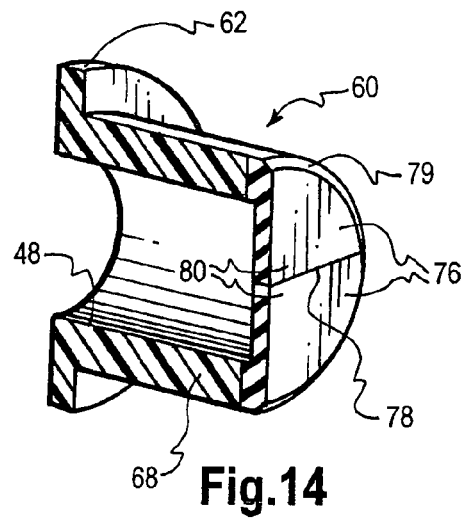
FIG. 14 is a perspective with parts shown in cross-section taken along lines 14-14 of FIG. 13.

With respect to FIGS. 11 and 12, a somewhat different cup-shaped outdwelling slit valve, generally designated 86, is illustrated, which comprises the previously mentioned flange 62 and central portion 68, as well as a distally extending convergingly-shaped tapered distal portion 79 and a distal tip 81. The cup-shaped slit valve 86 comprises a single two-way slit 83, which continuously traverses through the two oppositely sloped converging flats 82, across tip 81, and proximally beyond both flats 82 at two locations into the wall of the central portion 68. Slit 83 accommodates both infusion and aspiration at different rates.

Figure 15:
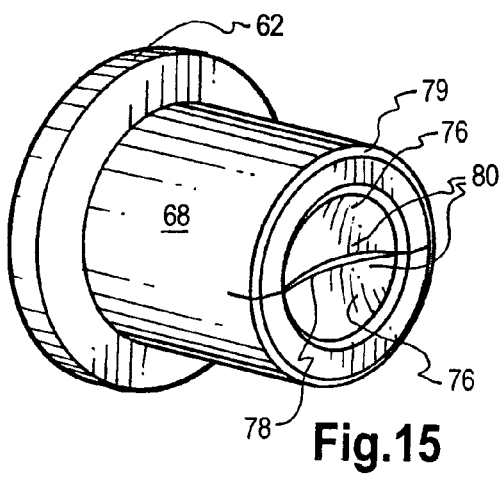
FIG. 15 is a perspective of the bulbous slit valve of FIG. 13, shown flexed so as to accommodate a lesser aspiration flow.
Figure 16:
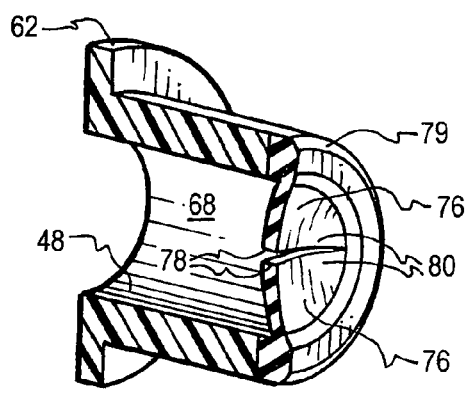
FIG. 16 is a perspective with parts shown in cross-section taken along lines 16-16 of FIG. 15.
Figure 17:
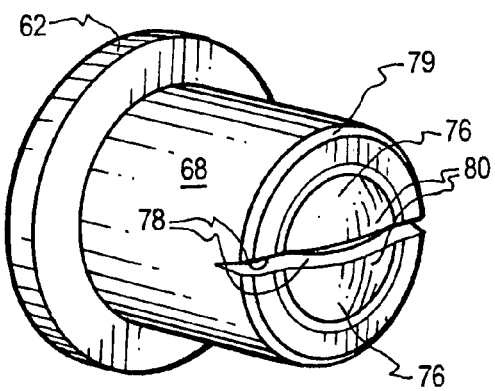
FIG. 17 is a perspective of the cup-shaped outdwelling slit valve of FIG. 13, shown flexed so as to accommodate a greater infusion flow.
Figure 18:
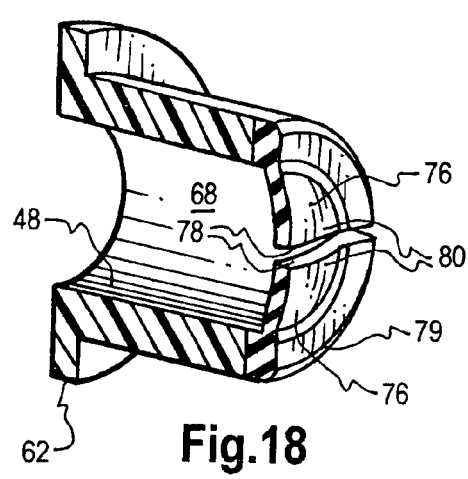
FIG. 18 is a perspective with parts shown in cross-section taken along lines 18-18 of FIG. 17.

FIGS. 9, 10 and 15-17 illustrate the manner in which each normally closed slit is flexed at respective pressure differential thresholds to accommodate infusion and aspiration, respectively. Specifically, as shown in FIGS. 9, 17 and 18, infusion fluid reaches a proximal pressure within the interior of the cup-shaped slit valve which, compared to the distal pressure on the slit valve, creates the necessary pressure differential threshold to accommodate opening of the slit by flexing the lips 80 away from their normally closed contiguous relation to the open condition illustrated in FIGS. 9, 17 and 18, accommodating infusion flow at a selected rate. The rate may be controlled to less than a maximum by spacing the slit 78 in question in close proximity to the adjacent housing surface.

To the contrary, when the distal pressure outside the cup-shaped slit valve exceeds the proximal pressure within the hollow interior of the cup-shaped sit valve by an amount equal to or greater than a predetermined threshold differential pressure, the lips of the slit will flex inwardly as shown in FIGS. 10, 15 and 16 to accommodate aspiration in a proximal direction.

Figure 19:
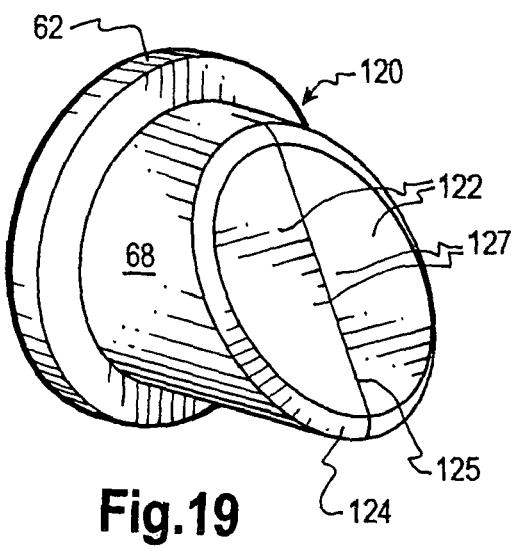
FIG. 19 is an enlarged perspective of a further outdwelling cup-shaped medical slit valve of the present invention.
Figure 20:
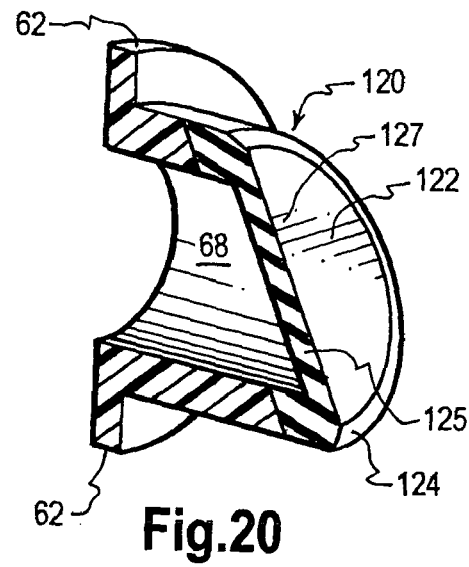
FIG. 20 is a perspective with parts shown in cross-section taken along lines 20-20 of FIG. 19.

Reference is now made to FIGS. 19 and 20, which illustrate a further cup-shaped outdwelling slit valve, generally designated 120, in accordance with principles of the present invention. Slit valve 120 comprises the previously described proximal flange 62 and hollow intermediate central cylindrical section 68, though somewhat truncated. The distal end of the slit valve 120 comprises a flat or planar diagonally-directed or beveled thin end wall 122 integrally joined at corner 124 to the cylindrical central section 68. End wall 122 comprises a normally closed slit 125, which extends centrally across the entire end wall 122 and also a short distance proximally, top and bottom, into the cylindrical wall 68. Thus, the end-to-end length of the slit 78 of FIGS. 19 and 20 exceeds the diameter of the cylindrical wall 68, thereby accommodating a large opening and a higher fluid flow rate when a pressure differential in either direction of a specific threshold causes the normally contiguous lips 127 of the slit 125 to flex away from each other and the normally closed slit 125 to open. A lesser aspirating rate or a greater infusion rate is then accommodated.

Figure 21:
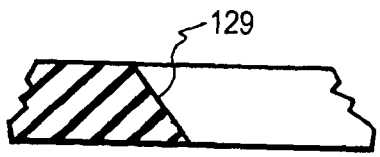
FIG. 21 is an enlarged cross section of a slit having a tapered end edge.
Figure 22:
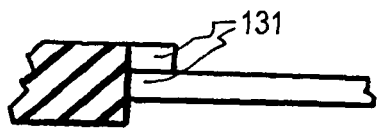
FIG. 22 is an enlarged cross section of a slit located in a flat having a greater surface area on one side than the other.

The influent verses effluent rate differential can be set at least in part by causing the slit to comprise angular end edges 129 as shown in FIG. 21. Also, the structure defining the end edges 131 of the slit as shown in FIG. 22 typically causes the slit ends to constrict during aspiration and to separate during infusion 131 so the flow path is large for infusion than aspiration.

From the foregoing it is clear to those skilled in the medical slit valve art that the distal section of the disclosed slit valves comprising at least one planar flat against which an influent-directed and effluent-directed pressure differential is imposed on interior and exterior parallel surfaces of each planar flat having a uniform thickness substantially less than the thickness of the central portion. Also, at least one normally closed slit is disposed in each planar flat extending between the exterior and interior surface thereof which slit comprises yieldable lips which selectively open to accommodate fluid flow through the slit in either of two directions, responsive to predetermined pressure differentials, in greater amounts when flow is in a distal direction than in a proximal direction.

It is preferred that the area of the interior surfaces of each planar flat is less than the area of the exterior surface of the flat. One to four flats may be used in each slit valve each flat having a normally closed slit disposed therein. Each planar flat may be located in the slit valve so as to be transversely disposed, or diagonally disposed or both transversely and diagonally disposed. It has been found that the superior results are gained when the normally closed slit extends beyond its planar flat into the central portion at one or both ends and where the thickness of the normally closed slit is less in the planar flat than in the central portion of the slit valve. The slit may bridge between two spaced flats across the distal tip of the slit valve.

The invention may be embodied in other specific forms without departing from the spirit of the central characteristics thereof. The present embodiments therefore are to be considered in all respects as illustrative and not restrictive, the scope of the invention being indicated by the appended claims rather than by the foregoing description, and all changes which come within the meaning and range of equivalency of the claims are therefore intended to be embrace therein.

What is claimed and desired to be secured by Letters Patent is:

1. An outdwelling cup-shaped one-piece medical slit valve, having a longitudinal axis, for use with a medical patient comprising:
    a one-piece body comprising:
        a hollow proximal flange, the flange being outwardly radially disposed away from the axis for securing the slit valve within a housing external of the patient; a hollow central valve portion comprising an intermediate valve section connected to and extending distally of the flange and comprising a wall defining a hollow interior, the wall comprising a substantially uniform thickness and a distal end;
        a normally closed distal valve section attached to the distal end of the wall of the intermediate valve section;
        the distal valve section comprising at least one planar flat comprising spaced parallel flat surfaces against which an influent-directed and effluent-directed pressure differential is imposed on the parallel surfaces of the at least one planar flat, the at least one planar flat having a thickness substantially less than the thickness of the region of the central valve portion immediately adjacent to the planar flat;
        at least one normally closed slit disposed in the at least one planar flat extending between the exterior and interior surface thereof which slit comprises normally closed yieldable lips which selectively open to accommodate fluid flow through the slit in either of two directions responsive to predetermined pressure differentials.

2. A medical slit valve according to claim 1 wherein the area of the interior surface of the at least one planar flat is less than the area of the exterior surface of the flat.

3. A medical slit valve according to claim 1 wherein the at least one planar flat is selected from the group consisting of one to four flats, each flat comprising a normally closed slit.

4. A medical slit valve according to claim 1 wherein the at least one planar flat is selected from the group consisting of those transversely disposed, those diagonally disposed and those both transversely and diagonally disposed.

5. A medical slit valve according to claim 1 wherein the at least one normally closed slit extends beyond the associated planar flat into the central portions at one or both ends.

6. A medical slit valve according to claim 1 wherein the distal section terminates in a distal tips selected from the group consisting of tips into which the slit extends and tips into which the slit does not extend.

7. A medical slit valve according to claim 6 wherein at least one planar flat comprises at least two spaced opposed planar flats and the tip comprises a tip into which the slit extend, the slit extending across both planar flats and across the tip.

8. A medical slit valve according to claim 1 wherein the thickness of the slit is greater at one or both ends thereof and lesser in the center thereof whereby proximally-directed aspirating pressure differential causes the greater thickness at one or both ends of the slit to forceful abut thereby restricting the degree to which the slit opens for lesser fluid flow but distally directed infusion pressure causes the greater thickness at one or both ends of the slit to separate thereby allowing the slit to fully open for greater fluid flow.

* * * * *